United States Patent [19]

Simon

[11] Patent Number: 5,051,109
[45] Date of Patent: Sep. 24, 1991

[54] PROTECTOR FOR CATHETER NEEDLE

[76] Inventor: Alexander Z. Simon, 4460 Ammon Rd., South Euclid, Ohio 44143

[21] Appl. No.: 552,934

[22] Filed: Jul. 16, 1990

[51] Int. Cl.$^5$ .......................... A61M 5/00; A61M 5/32
[52] U.S. Cl. .................................... 604/263; 604/192
[58] Field of Search ............... 604/110, 162, 167, 192, 604/198, 263

[56] References Cited

U.S. PATENT DOCUMENTS

| | | | |
|---|---|---|---|
| 3,134,380 | 5/1964 | Armao | 128/215 |
| 3,658,061 | 4/1972 | Hall | 604/192 |
| 4,329,989 | 5/1982 | Dallons et al. | 128/218 R |
| 4,636,201 | 1/1987 | Ambrose et al. | 604/192 |
| 4,725,267 | 2/1988 | Vaillancourt | 604/192 |
| 4,735,618 | 4/1988 | Hagen | 604/192 |
| 4,762,516 | 8/1988 | Luther et al. | 604/164 |
| 4,775,369 | 10/1988 | Schwartz | 604/263 |
| 4,795,443 | 1/1989 | Permenter et al. | 604/198 |
| 4,804,371 | 2/1989 | Vaillancourt | 604/198 |
| 4,834,718 | 5/1989 | McDonald | 604/195 |
| 4,850,977 | 7/1989 | Bayless | 604/198 |
| 4,863,434 | 9/1989 | Bayless | 604/198 |
| 4,863,435 | 9/1989 | Sturman et al. | 604/198 |
| 4,892,521 | 1/1990 | Laico et al. | 604/192 |
| 4,955,866 | 9/1990 | Corey | 604/263 |
| 4,978,344 | 12/1990 | Dombrowski | 604/263 |

FOREIGN PATENT DOCUMENTS

| | | | |
|---|---|---|---|
| 8910767 | 11/1989 | World Int. Prop. O. | 604/263 |
| 9000075 | 1/1990 | World Int. Prop. O. | 604/263 |

Primary Examiner—C. Fred Rosenbaum
Assistant Examiner—Sharon Finkel
Attorney, Agent, or Firm—Body, Vickers & Daniels

[57] ABSTRACT

A protector for needle apparatus which includes a conventional catheter slidingly receiving a needle. The catheter has a hub portion at its distal end which is initially adjacent the needle portion. An especially configured guard housing has an open ended, cylindrical base portion which slidably receives the catheter's hub portion and a closable front wall which is resiliently biased into an open position when the guard housing is positioned over the catheter hub. A tether between the guard housing and needle handle permits the needle, after puncture, to be withdrawn into the base portion of the guard when the tether pulls the guard off the catheter hub at which point the front wall closes the opening of the base portion to prevent inadvertent needle puncture.

15 Claims, 2 Drawing Sheets

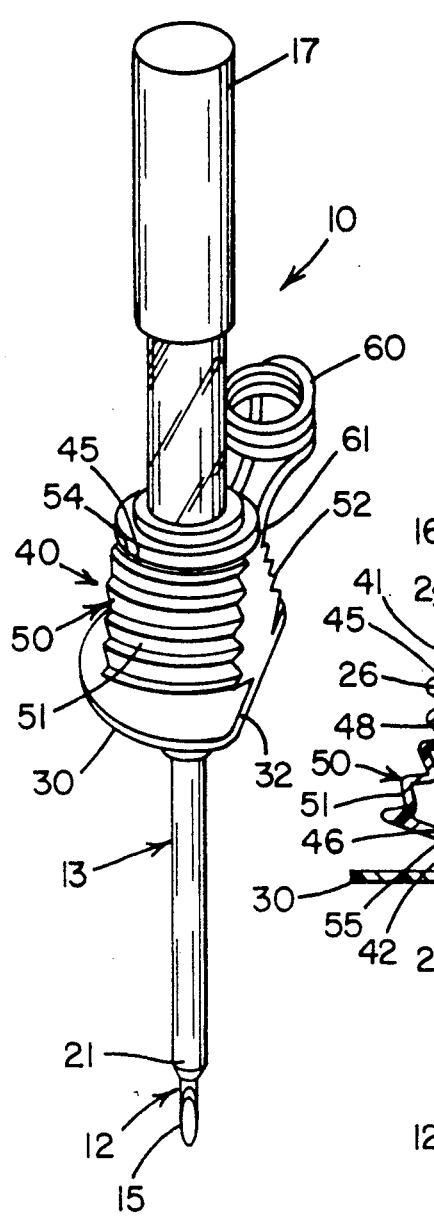
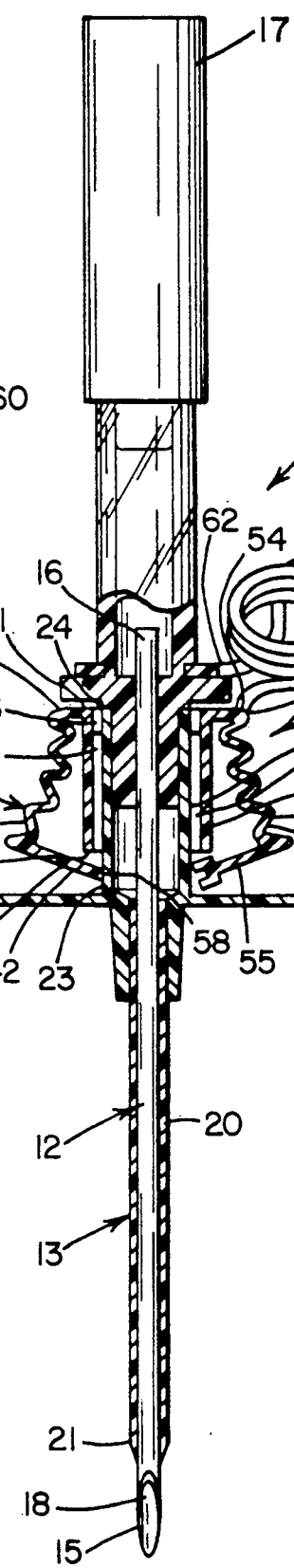
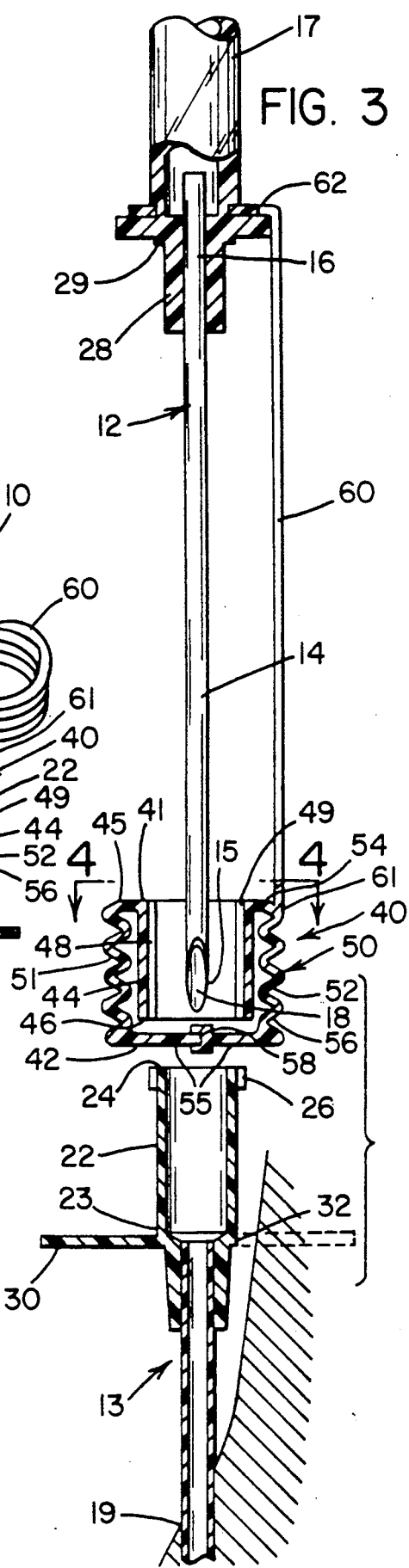

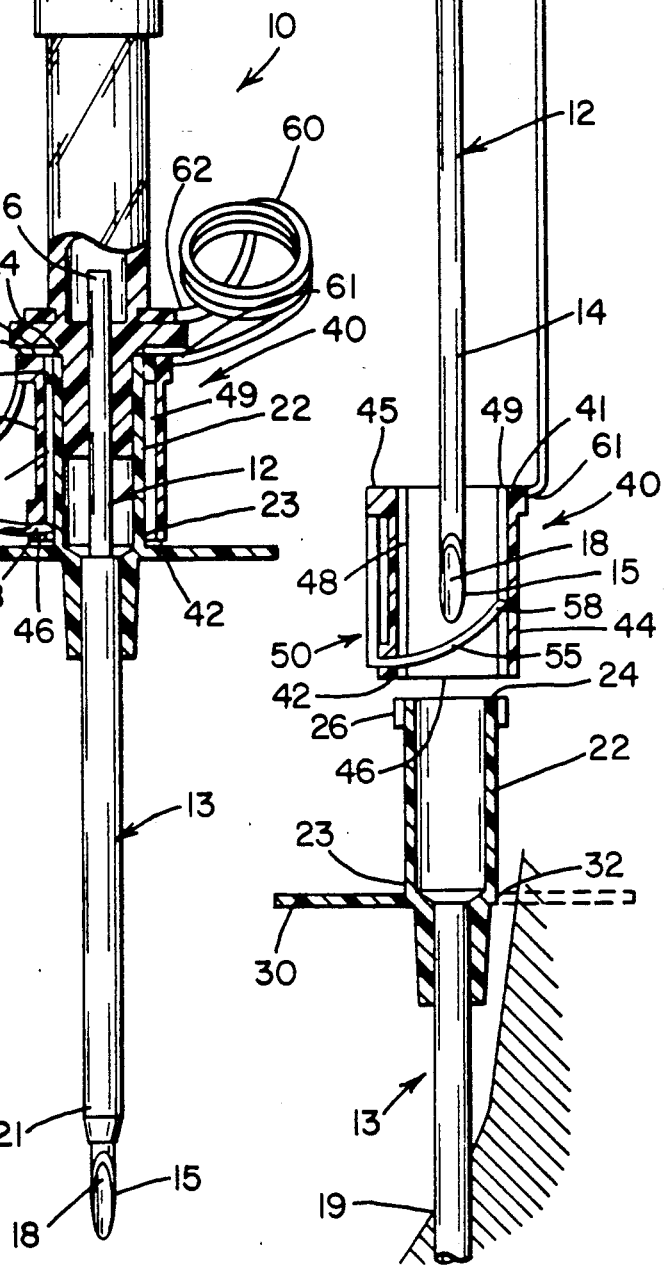

PROTECTOR FOR CATHETER NEEDLE

This invention relates generally to an improvement in medical needles of the catheter type and more particularly to a protective device for preventing accidental needle puncture after use.

INCORPORATION BY REFERENCE

Luther et al U.S. Pat. No. 4,762,516 dated Aug. 9, 1988 and McDonald U.S. Pat. No. 4,834,718 dated May 30, 1989 are incorporated herein by reference and made a part hereof so that the specifications hereof need not define in detail conventional material known in the prior art.

BACKGROUND OF THE INVENTION

The concern over acquired immune deficiency syndrome (AIDS) and other infectious diseases such as hepatitis has resulted in a number of protective devices designed to prevent accidental puncture to clinical personnel after use of a medical needle. Most of the protective devices have been developed for hypodermic needles as opposed to needles of the type to which the present invention relates. Medical apparatus employing needles of the type to which the present invention relates typically comprise a hollow inner needle which has a cutting or pointed edge for puncture and a concentric cylindrical device which slidingly receives the hollow needle. Typically, the outer cylindrical device is a catheter although the outer device could be the outer cannula of a biopsy needle. In needles of this type, the puncture is made with one hand similar to that of a hypodermic needle, but the withdrawal of the needle from the puncture site is made with two hands thus raising the likelihood of accidental needle puncture resulting from clinical personnel holding the catheter in a precise position while the needle is withdrawn.

The prior art has recognized the difficulties associated with catheters and has developed fail safe, puncture-proof devices as disclosed in the '516 and '718 patents incorporated by reference herein. Basically, the prior art devices modify the needle so that the needle is encased in a telescoping tubular arrangement. The needle conventionally punctures the patient's skin in a non-telescoped position. To withdraw the needle after puncture, the clinician grabs one end of the device while retracting the handle portion to telescope the handle so that the needle when withdrawn is retained within the expanded handle.

The prior art devices are effective but have not achieved wide scale commercial success principally because the cost of constructing a long, two-piece telescoping handle arrangement, even with relatively inexpensive plastics, materially increases the cost of the device compared to conventional, unshielded catheter needles. In addition, the prior art protective needles are more cumbersome to operate which may or may not be overcome with familiarity. Basically, the clinician prefers to advance the catheter with one hand while the needle is withdrawn with the other hand. In the prior art devices, the clinician must hold the telescoping barrel, sometimes by special or awkwardly placed tabs on the barrel. Although the barrel is fitted to the catheter hub, the point is that the attention of the clinician is focused away from the catheter while the needle is removed and the hand position is somewhat awkward. This can present problems in emergency situations, typically outside the confines of the hospital, where the catheter must be administered quickly.

SUMMARY OF THE INVENTION

Accordingly, it is a principal object of the invention to provide a fail safe protector for needle apparatus for administering catheters and the like which overcomes the prior art disadvantages discussed above.

This object along with other features of the invention is achieved in a medical needle apparatus of the catheter type which includes a hollow needle having a cutting edge at its proximal end for effecting a puncture, a handle portion at its distal end and a cylindrical body portion between its ends. A catheter having a forward end initially adjacent said needle's cutting edge, a hub portion at its distal end initially adjacent said needle's handle portion and a cylindrical body portion between its ends slidably receives the needle's cylindrical body portion. A hollow, elongated protector guard housing is initially positioned to slidingly receive the catheter's hub portion. The guard housing has a rearward end initially adjacent the needle's handle, a closable forward end and a resilient mechanism extending from at least one of the guard housing ends which biases the forward end from an open to a closed position. A tether secured between the guard housing and the handle portion of the needle permits the guard housing to remain on the catheter while the needle is withdrawn from the catheter and then separate from the catheter's hub portion when the needle's cutting end is withdrawn from the catheter's hub to permit the resilient mechanism to bias the forward end of the guard housing to its closed position whereby the cutting edge of the needle is contained within the guard housing while the tether means prevents the needle's cutting edge from being withdrawn from the guard housing thus preventing accidental puncture from the needle after use.

In accordance with a more specific feature of the invention, the protector guard housing has an open ended, cylindrical base portion concentric with the catheter's hub portion and contiguously extending from the rearward end of the guard housing toward the forward end. The cylindrical base portion has diametrically opposed, radially outwardly extending notches formed therein and the catheter hub portion has diametrically opposed, radially extending locking ears so that the ears are received within the notches of the base portion when the guard housing is initially positioned on the catheter hub to permit the guard housing to slide off the hub and the cylindrical base to receive the needle when the needle is withdrawn from the catheter. The guard housing has a resilient side wall portion contiguous with its rearward end and also with the forward end and the side wall is displaced radially outwardly from the guard's base portion. The guard's forward end is defined by a sealable front wall portion which is contiguous with the side wall and the front wall covers at least a portion of the cylindrical opening at the forward end of the cylindrical base portion when the guard housing slides off the catheter base to prevent puncture by the needle's cutting edge. The front wall is displaced radially outwardly by contact with the catheter's hub portion in the initial position whereat the base portion slidingly engages the catheter hub so that the side wall is effective to resiliently bias the front wall to its closed position while simultaneously and to a lesser extent biasing the base portion into contact with the catheter's hub portion thereby insuring a sliding engagement between the guard housing and the catheter hub so that the guard is not inadvertently pulled from the hub prematurely. The side wall is preferably discontinuous and extends circumferentially about the catheter's hub portion a distance which subdivides an arc of at least about 90° and two diametrically opposed side wall segments may be provided with each containing a front wall segment which can interlock with one another when snapped to their closed position.

In accordance with yet another aspect of the invention, the side wall is curved in its open position and provided with V-shaped ridges or a sinusoidal shaped wave pattern to increase the resilient biasing force and insure snapping of the front wall into its closed position even if the plastic material in the guard housing should take a set due to heat resulting from the storage environment or the long time during which the needle may be stored.

In accordance with another aspect of the invention, the tether may simply comprise a cord of a length equal to the length of the intermediate portion of the needle and the length of the base portion of the guard must be at least equal to the diameter of the base portion to prevent dislodgement of the needle from the base portion. Optionally, the cord can be provided with an elastic portion to bias the cutting edge of the needle into contact with the front wall after needle removal. Alternatively, the tether can comprise an integral, relatively wide plastic ribbon which is formed as part of the guard housing in the shape of a single coil which is unwound when the needle is withdrawn from the catheter to maintain the guard housing affixed to the hub and assist in withdrawing the needle from the catheter.

In accordance with the improvement aspect of the invention, a conventional needle and a conventional catheter is provided with a guard housing having an open ended cylindrical base portion receiving the hub portion of the catheter in an initial position of the device and slidingly removable from the catheter when the needle is withdrawn. The guard housing has a closable front wall having an initial position whereat the front wall is removed from the base portion when the guard housing is positioned on the hub portion and a closed position where the front wall is positioned over one end of the base portion. The guard housing has a side wall contiguous with the base portion biasing the front wall to its closed position. A tether is affixed at one end to the guard housing and at its other end to the needle handle and is of a length sufficient to permit the needle end to be withdrawn from the catheter hub but insufficient to prevent the needle end from being withdrawn from the open end of the base portion of the guard whereby the needle end is maintained within said guard housing to prevent inadvertent puncture therefrom.

It is thus an object of the present invention to provide a guard housing for needle apparatus which prevents accidental puncture from the cutting end of the needle after use.

It is another object of the invention to provide a protector for a medical needle to prevent puncture from the cutting end of a needle which is simple and economical.

Yet another object of the invention is to provide a guard for preventing inadvertent puncture by a catheter needle apparatus which can be applied to existing designs of needle catheters.

Yet another object of the invention is to provide a guard to prevent inadvertent puncture after use from a needle catheter apparatus which can be inserted and withdrawn from the patient with the same motion and same hand position as that currently used in conventional catheter needle apparatus.

Yet another object of the invention is to provide a plastic protector guard for catheter needle type apparatus which retains its resilient closure action not withstanding storage of the needle over long periods of time or storage of the needle in warm environments.

These and other objects of the present invention will become apparent to those skilled in the art upon reading and understanding the detailed description of the invention as set forth in the section below.

BRIEF DESCRIPTION OF THE DRAWINGS

The invention may take form in certain parts and arrangement of parts, a preferred embodiment of which will be described in detail and illustrated in the accompanying drawings which form a part hereof and wherein:

FIG. 1 is a pictorial plan view of an I.V. catheter apparatus of the present invention;

FIG. 2 is a partially sectioned, plan view of the apparatus of the present invention in its initial, unapplied position;

FIG. 3 is a partially sectioned, elevation view of the apparatus shown in FIG. 2 but with the apparatus in its withdrawn position;

FIG. 4 is an end view of the guard protector of the invention taken along lines 4—4 of FIG. 3;

FIG. 5 is a top view of the guard protector shown in FIG. 4;

FIG. 6 is a front view of the guard protector shown in FIG. 5;

FIG. 7 is a partially sectioned, plan view of an alternative embodiment of the invention with the needle catheter apparatus in its initial position; and FIG. 8 is a partially sectioned, plan view of the alternative embodiment of the invention showing the needle catheter in its withdrawn position.

DETAILED DESCRIPTION OF THE PREFERRED EMBODIMENT

Referring now to the drawings wherein the showings are for the purpose of illustrating preferred embodiments of the invention only and not for the purpose of limiting the same, there is shown FIGS. 1 through 3 an intravenous needle-catheter assembly generally designated by reference numeral 10 which basically includes a needle 12 and a catheter 13.

Needle 12 is hollow and has a cutting end 15 which could be simply a sharp pointed end, a rearward end 16 which is encased or embedded in a plastic handle 17 and an intermediate hollow tubular portion 18 in between cutting end 15 and rearward end 16. Needle 12 is used to effect tissue puncture at a site 19 in a conventional manner, for backdrawing blood through needle 12 and for the purpose of inserting catheter 13 into the site such as at a vein. Needle 12 is typically made of a steel alloy.

Catheter 13 is flexible and is conventional. Catheter 13 may be viewed as a cylindrical member concentric with needle 12 and slidingly receiving needle 12 therein and has a flexible, cylindrically hollow portion 20 with a forward edge 21 adjacent needle cutting edge 15 and a hub portion 22 at its rearward end. Actually, hub portion 22 and cylindrical portion 20 are separate plastic pieces which are press fitted together but will be referred to as portions of catheter 13 herein for terminology purposes. For definitional purposes, hub portion 22 has a forward end 23 and a rearward end 24. At rearward end 24 on the outside surface of hub portion 22 is a conventional catheter fitting 26 which remains outside the patient's body and is used for connecting a source for intravenous medication to the catheter. Catheter fitting 26 is conventionally referred to as a luer-type locking fitting and will be referred to herein as a pair of diametrically opposed radially extending ears protruding from the outside surface of hub portion 22 at rearward end 24 thereof. Needle handle 17 has a boss 28 which extends from an annular shoulder 29 with rearward end 16 of needle 12 embedded within boss 28 as shown. Boss 28 has a cylindrical outer surface defined by an outside diameter which approximates the inside diameter of hub portion 22 thus permitting boss 28 to snugly and slidably fit within the inside surface of hub portion 22 with annular shoulder 29 abutting rearward end 24 of hub portion 22 thus providing a rigid connection between catheter 13 and needle 12 permitting catheter insertion at the puncture site, etc.

Adjacent forward end 23 of hub portion 22 is a modified finger-tape support tab 30 which is best shown in FIG. 1. Tab 30 extends radially outwardly from hub portion 22 and circumscribes hub portion 22 through an included angle of about 180° whereat tab 30 stops at flat edge 32 which is aligned with the outside surface of hub portion 22. Flat edge 32 allows catheter 13 to lie flat against the patient's skin while tab 30 also permits strips of tape to be wrapped around the tab for taping catheter 13 in place at the site. Additionally, tab 30 permits holding catheter 13 in place while needle 12 is withdrawn. Except for tab 30 which is an optional modification, catheter 13 and needle 12, as thus far described, are entirely conventional and commercially available.

The invention includes an elongated, protective guard housing 40 adapted to snugly and slidingly engage hub portion 22 of catheter 13. Protector guard housing 40 has a rearward end 41 and a forward end 42. In the initial, as supplied position of catheter assembly 10 as shown in FIG. 2, rearward end 41 is adjacent rearward end 24 of hub portion 22 and forward end 42 is adjacent forward end 23 of catheter hub portion 22. Contiguous with and extending from rearward end 41 of guard housing 40 is an open ended, cylindrical base portion 44 which, consistent with terminology used herein, has a rearward end 45 and a forward end 46. Cylindrical base portion 44 has an inside diameter which is sized to snugly engage in a slidable manner hub portion 22 of catheter 13. As best shown in FIGS. 4-6, cylindrical base portion 44 is not formed as a true cylinder in that a pair of diametrically opposed, radially outwardly extending flats or notches 48, 49 which extend the length of base portion 44 (FIGS. 2, 7) are provided. Notches 48, 49 receive the ears of catheter fitting 26 and permit cylindrical base portion 44 to slide onto and off of catheter hub portion 22. Importantly, notches 48, 49 fix the circumferential position of protector guard housing 40 relative to catheter hub portion 22 so that the length of the tether (to be described) can be accurately fixed. Also contiguous with and extending from guard housing rearward end 41 is a side wall portion 50. In the preferred embodiment shown in FIGS. 1 through 6, side wall portion 50 comprises two diametrically opposed side wall segments 51, 52. Each side wall segment 51, 52 has a rearward end 54, a closable front wall 55 and a body portion 56 and the description of one segment will be sufficient to likewise describe the other segment and also, in general, side wall portion 50. Protector guard housing 40 is made of any relatively rigid but flexible plastic. Closable front wall 55 as best shown in FIG. 3 (and FIG. 6) has a length which when body portion 56 is parallel with cylindrical base portion 44 will cover all or a portion of the opening adjacent forward end 46 of cylindrical base portion 44. The exposed edge 58 of front wall 55 contacts the outside surface of hub portion 22 when protector guard housing 40 is fitted over catheter hub portion 22 and in the process thereof bends and stresses body portion 56 and the prestress thus applied to body portion 56 enables body portion 56 to resiliently snap closable front wall 55 over the opening at forward end 46 of cylindrical base portion 44. Body portion 56 is formed with either V-shaped ridges or a sinusoidal wave pattern which in turn is flexed when open edge 58 contacts catheter hub portion 22 in the initial position of protective guard housing 40.

In the preferred embodiment, exposed edge 58 as best shown in FIGS. 4 and 6 is flat and body portion 56 of each side wall segment 51, 52 is formed as a segment, preferably an arcuate segment, which circumscribes cylindrical base portion 44 a distance subtended by an arc of at least 90°. In the preferred embodiment employing side wall segments 51, 52, exposed edge 58 of one front wall 55 is formed in a locking received exposed edge 58 of the other side wall segment 51 or 52 as best shown in FIG. 3. Alternatively, the lengths of front wall 55 of both side wall segments 51, 52 can be increased from the body and the length of the one of the body portions 56 decreased so that front wall 55 of both side wall segments 51, 52 simply overlap. Other variations in configuration of front wall 55 which are sufficient to close the opening at forward end 46 of cylindrical base portion 44 can be employed.

A tether 60 is secured at one end 61 to guard housing 40 and at its opposite end 62 to needle handle 17. Tether 60 is a cord mechanically affixed to guard housing 40 and needle handle 17 and optionally provided with an elastomer portion (not shown) over a discrete portion of its length. Alternatively, tether 60 could be a plastic line such as a fishing line and applied to protective guard housing 40 and needle handle 17 by heat. Alternatively, tether 60 could be molded as a thin flat ribbon and as a part of protector guard housing 40. Specifically, tether 60 could be molded as a single turn coil with a circumference equal to the length of intermediate hollow tubular portion 18 of needle 12. The free end of the ribbon tether (not shown) could be thermally attached or bonded to handle 17 of needle 12. The hoop stress or uncoiling force of the single turn ribbon would assist in maintaining guard housing 40 on catheter hub 22 during needle withdrawal. However, this is not absolutely necessary and is mentioned in the sense of an alternative construction.

The operation of catheter assembly 10 is readily apparent from the drawings. Catheter assembly 10 is supplied and removed from its package in its initial configuration shown in FIG. 2. The puncture at site 19 is made in the same manner and with the same hand position as that used in the conventional catheter assembly. The resilient force established by body portion 56 through contact by exposed edge 58 with hub portion 22 assures that protective guard housing 40 remains with hub portion 22. Flexure of body portion 56 to some extent flexes base portion 44 and to prevent any inadvertent premature removal of guard housing 40, base portion 44 could be slitted (not shown) along its length so that flexure of front wall 55 establishes frictional contact with hub portion 22 not only at exposed edge 58 but also by contact with base portion 44. Once the puncture is made, needle 12 is withdrawn from catheter 13 in exactly the same manner as done with the conventional catheter. The clinician places one hand on hub portion 22 and with his or her other hand on handle 17, withdraws needle 12 from catheter 13. Attention can be focused on catheter 13 to insure catheter 13 remains entirely stationary at the site. As needle 12 is withdrawn, tether 60 begins to expand from its contracted position shown in FIG. 2 to the stretched position shown in FIG. 3. As soon as cutting end 15 of needle 12 passes inwardly of forward end 46 of cylindrical base portion 44, tether 60 becomes fully extended and further retraction of needle 12 pulls base portion 44 over hub portion 22. As soon as forward end 46 of base portion 44 clears rearward end 24 of hub portion 22, the resiliency of body portion 56 will snap front wall 55 into the closed position shown in FIG. 3. At this point, cutting end 15 of needle 12 is completely encased within cylindrical body portion 44 which is inaccessible except for its openings at its rearward and forward ends 45, 46. Front wall 55 has closed access to forward end 46 of base portion 44. Rearward end 45 of base portion 44 is open but because of the size of the diameter of cylindrical base portion 44 it is not possible for the clinician or anyone who may come in contact with the needle at any time prior to its placement into specially designed bio-hazard containers to contact the needle's cutting edge 15. It is also noted that the standard I.V. line uses a standard dimensioned catheter which is of a size that prevents finger insertion from rearward end 45. In order to prevent the needle's cutting edge 15 from being withdrawn from rearward end 45 of cylindrical base portion 44, the length of cylindrical base portion 44 must be at least as great as its internal diameter. Also, because of the position of notches 48, 49 engaging the ears of catheter fitting 26, the position of protector guard housing 40 relative to catheter hub portion 22 is fixed so that guard housing 40 does not rotate relative to hub portion 22 which could otherwise shorten the effective length of tether 60 resulting in the clinician having to tug needle 12 from catheter 13 just at the point where cutting end 15 has to clear forward end 46 of cylindrical bore portion 44. Thus, a smooth removal is assured.

An alternative embodiment is disclosed in FIGS. 7 and 8 and reference numerals used to designate parts and components of catheter assembly 10 in the preferred embodiment will likewise apply to the same parts and components if applicable in the alternative embodiment. In the alternative embodiment, only one side wall portion 50 is used. Adjacent forward end 46 of cylindrical base portion 44 is a slot 70 through which a front wall 55 extends so that exposed edge 58 directly contacts catheter hub portion 22. When needle 12 is removed from catheter 13 in its withdrawn position shown in FIG. 8, front wall 55 will extend through slot 70 and close forward end 46 of cylindrical base portion 44. Slot 70 can be straight or curved, but if curved, front wall 55 will likewise be curved. Also, a second slot can be added and a second wall with another side wall segment used in conjunction therewith.

The invention has been described with reference to a preferred and alternative embodiment. Obviously, modifications and alterations will occur to those skilled in the art upon reading and understanding a description of the invention disclosed herein. For example, the invention has been described with reference to an intravenous catheter needle apparatus. Such apparatus can be characterized broadly as an inner cylinder concentrically disposed within an outer cylinder and with one of the cylinders having at least a cutting end. This feature is shared with biopsy needles particularly with those biopsy needles which leave one of the cannulas at the puncture site. The invention is particularly suited for such application because guard housing 40 will protect against puncture upon withdrawal in the manner described while the tether 60 can be severed at the lab to remove the biopsy specimen. Thus, reference herein and in the claims to apparatus of the catheter type is intended to cover all such applications. Further, it is intended to include all such modifications and alterations insofar as they come within the scope of the invention.

Having thus defined the invention, the following is claimed:

1. A medical needle apparatus of the catheter type for preventing accidental puncture, said catheter type needle comprising:

a hollow needle having a cutting edge at its proximal ed for effecting a puncture, a handle portion at its distal end and a cylindrical body portion between its ends;

a catheter having a forward end initially adjacent said needle's cutting edge, a hub portion at its distal end initially adjacent said needle's handle portion and a cylindrical body portion between its ends, said catheter slidably receiving said needle's cylindrical body portion;

a hollow protector guard housing having a rearward end initially adjacent said needle's handle, a hollow tubular base portion extending from said rearward end and concentric with said hub portion for initially slidably receiving said hub portion; a closable forward end initially laterally outwardly of said hub portion, and adapted, in its closed position, to cover the forward opening of said tubular base portion; and resilient spring means extending from at least one of said guard housing ends biasing said forward end radially inwardly to its closed position for frictionally maintaining said guard housing on said hub portion initially and subsequently moving said forward end to its closed position; and tether means secured between said guard housing and said handle portion of said needle permitting said guard housing to remain on said catheter while said needle is withdrawn from said catheter and causing said guard housing to separate from said catheter's hub portion when said needle's cutting end is withdrawn from said catheter's hub to permit said resilient means to automatically spring said forward end of said guard housing to its closed position whereby said cutting edge is irretrievably contained within said base portion while said tether means also prevents said cutting edge from being withdrawn from said guard housing thus preventing accidental puncture from said needle after use.

2. The apparatus of claim 1 wherein said base portion being cylindrical and having diametrically opposed radially outwardly extending notches formed therein, said catheter hub portion having diametrically opposed, radially extending, conventionally-standard catheter locking ears, said ears received within said notches when said guard housing is initially positioned on said catheter hub to assume said cylindrical base is pulled linearly off said hub portion without rotation to minimize any tendency of said tether means to foul itself and assure smooth retraction of said needle.

3. The apparatus of claim 2 wherein said guard housing has a resilient side wall portion contiguous with said rearward and forward ends of said guard housing, and displaced radially outwardly from said guard's base portion; said guard's forward end defined by a sealable front wall contiguous with said side wall, said front wall covering at least a portion of the forward opening of said cylindrical base portion when said guard housing slides off said catheter's hub portion to prevent puncture by said needle's cutting edge and said front wall displaced radially outwardly by said catheter's hub portion when said base portion slidingly engages said catheter hub whereby said side wall resiliently biases said front wall to its closed position and simultaneously biases said base portion into contact with said hub portion to insure sliding engagement between said guard housing and said catheter hub whereby said guard is maintained in its initial position.

4. The apparatus of claim 3 wherein said side wall is discontinuous and extends circumferentially about said catheter's hub portion a distance which subtends an arc of at least about 90°.

5. A medical needle apparatus of the catheter type comprising:
   a hollow needle having a cutting edge at its proximal end for effecting a puncture, a handle portion at its distal end and a cylindrical body portion between its ends;
   a catheter having a forward end initially adjacent said needle's cutting edge, a hub portion at its distal end initially adjacent said needle's handle portion and a cylindrical body portion between its ends, said catheter slidably receiving said needle's cylindrical body portion;
   a hollow protector guard housing initially positioned to slidingly receive said catheter's hub portion, said guard housing having a rearward end initially adjacent said needle's handle, a closable forward end initially laterally outwardly of said hub portion, and resilient means extending from at least one of said guard housing ends biasing said forward end radially inwardly to its closed position;
   said guard housing having a cylindrical base portion concentric with said catheter's hub portion and contiguous with said rearward end of said guard housing; said cylindrical base portion having diametrically opposed, radially outwardly extending notches formed therein; said catheter hub portion having diametrically opposed, radially extending locking ears, said ears received within said notches when said guard housing is initially positioned on said catheter hub and said cylindrical base receiving said needle when said needle is withdrawn from said catheter; and
   said guard housing having a resilient side wall portion contiguous with said rearward and forward ends of said guard housing, and displaced radially outwardly from said guard's base portion; said guard's forward end defined by a sealable front wall contiguous with said side wall, said front wall covering at least a portion of the forward opening of said cylindrical base portion when said guard housing slides off said catheter's hub portion to prevent puncture by said needle's cutting edge and said front wall displaced radially outwardly by said catheter's hub portion when said base portion slidingly engages said catheter hub whereby said side wall resiliently biases said front wall to its closed position and simultaneously biases said base portion into contact with said hub portion to insure sliding engagement between said guard housing and said catheter hub;
   said side wall being discontinuous and extending circumferentially about said catheter's hub portion a distance which subtends an arc of at least about 90°; said side wall being formed with sinusoidal shaped waves which are flexed when said front wall contacts said hub portion to increase the rigidity and biasing force of said side wall; and
   tether means secured between said guard housing and said handle portion of said needle permitting said guard housing to remain on said catheter while said needle is withdrawn from said catheter and separate from said catheter's hub portion when said needle's cutting end is withdrawn from said catheter's hub to permit said resilient means to bias said forward end of said guard housing to its closed position whereby said cutting edge is contained within said guard housing while said tether means prevents said cutting edge from being withdrawn from said guard housing thus preventing accidental puncture from said needle after use.

6. The apparatus of claim 4 wherein said side wall is flexed in an arcuate shape when said front end is resting on said catheter hub.

7. The apparatus of claim 1 wherein said tether means is a plastic ribbon having a discrete width and formed as a single coil when said apparatus is in its initial position to prevent tanglement with said needle upon needle withdrawal.

8. The apparatus of claim 1 wherein said tether is a cord.

9. The apparatus of claim 8 wherein said cord has an elastic portion thereof, said elastic portion stretched when said cutting edge leaves said catheter's hub portion whereby contact with said forward end is assured.

10. The apparatus of claim 4 wherein said side wall circumferentially extends said distance in an arcuate shape.

11. A medical needle apparatus of the catheter type comprising:
   a hollow needle having a cutting edge at its proximal end for effecting a puncture, a handle portion at its distal end and a cylindrical body portion between its ends;
   a catheter having a forward end initially adjacent said needle's cutting edge, a hub portion at its distal end initially adjacent said needle's handle portion and a cylindrical body portion between its ends, said catheter slidably receiving said needle's cylindrical body portion;
   a hollow protector guard housing initially positioned to slidingly receive said catheter's hub portion, said guard housing having a rearward end initially adjacent said needle's handle, a closable forward end initially laterally outwardly of said hub portion, and resilient means extending from at least one of said guard housing ends biasing said forward end radially inwardly to its closed position;
   said guard housing having a cylindrical base portion concentric with said catheter's hub portion and contiguous with said rearward end of said guard housing; said cylindrical base portion having diametrically opposed, radially outwardly extending notches formed therein; said catheter hub portion having diametrically opposed, radially extending locking ears, said ears received within said notches when said guard housing is initially positioned on said catheter hub and said cylindrical base receiving said needle when said needle is withdrawn from said catheter; and said guard housing having a resilient side wall portion contiguous with said rearward and forward ends of said guard housing, and displaced radially outwardly from said guard's base portion; said guard's forward end defined by a sealable front wall contiguous with said side wall, said front wall covering at least a portion of the forward opening of said cylindrical base portion when said guard housing slides off said catheter's hub portion to prevent puncture by said needle's cutting edge and said front wall displaced radially outwardly by said catheter's hub portion when said base portion slidingly engages said catheter hub whereby said side wall resiliently biases said front wall to its closed position and simultaneously biases said base portion into contact with said hub portion to insure sliding engagement between said guard housing and said catheter hub; said side wall portion being circumferentially discontinuous and includes a first and second, diametrically-opposed side wall segment, each side wall segment extending circumferentially about said base portion no more than 180° and each side wall segment having a front wall segment, said front wall segments interlocking with one another when said guard housing is pulled from said catheter hub; and tether means secured between said guard housing and said handle portion of said needle permitting said guard housing to remain on said catheter while said needle is withdrawn from said catheter and separate from said catheter's hub portion when said needle's cutting end is withdrawn from said catheter's hub to permit said resilient means to bias said forward end of said guard housing to its closed position whereby said cutting edge is contained within said guard housing while said tether means prevents said cutting edge from being withdrawn from said guard housing thus preventing accidental puncture from said needle after use.

12. The apparatus of claim 3 further including said catheter hub portion having a rearward end and a forward end, said rearward end initially adjacent said needle's handle, a radially extending tab protruding from said hub adjacent said forward end of said catheter hub portion, said tab circumferentially extending about said hub portion no more than 180° whereby said tab is held by one hand, advance and to retain the catheter in place at the site while said needle is withdrawn therefrom while also functioning as a tape support surface to maintain said catheter flat against the skin at said puncture site.

13. The apparatus of claim 8 wherein said cord has a free length equal to the length of said intermediate portion of said needle, and said base portion of said guard housing has a length greater than its diameter whereby said needle's cutting end is prevented by said cord from leaving said base portion and said diameter of said base portion is of a size to prevent finger insertion through the open rearward end thereof.

14. In an intravenous catheter apparatus having a needle with a handle for effecting a puncture at a site on a patient and a catheter with a hub initially adjacent said handle which is to be left at the puncture site for intravenous feeding and like applications after said needle is removed, the improvement comprising:

a guard housing having an open ended, cylindrical base portion receiving said hub portion in an initial, unapplied position of said device and slidingly removable from said hub when said needle is withdrawn from said catheter after site puncture, a closable front wall having an open position where said front wall is removed form said base portion when said guard housing is in its initial position and a closed position where said front wall is positioned over one end of said base portion when said needle is fully withdrawn from said catheter, and means affixed to said base portion biasing said front wall to its closed position;

said guard housing having a resilient side wall portion contiguous with said rearward and forward ends of said guard housing, and displaced radially outwardly from said guard's base portion; said guard's forward end defined by a sealable front wall contiguous with said side wall, said front wall covering at least a portion of the forward opening of said cylindrical base portion when said guard housing slides off said catheter's hub portion to prevent puncture by said needle's cutting edge and said front wall displaced radially outwardly by said catheter's hub portion when said base portion slidingly engages said catheter hub whereby said side wall resiliently biases said front wall to its closed position and simultaneously biases said base portion into contact with said hub portion to insure sliding engagement between said guard housing and said catheter hub;

said protector guard housing having a cylindrical base portion concentric with said catheter's hub portion and contiguous with said rearward end of said guard housing; said cylindrical base portion having diametrically opposed, radially outwardly extending notches formed therein, said catheter hub portion having diametrically opposed, radially extending locking ears, said ears received within said notches when said guard housing is initially positioned on said catheter hub and said cylindrical base receiving said needle when said needle is withdrawn from said catheter; said side wall being formed with sinusoidal shaped waves which are flexed when said front wall contacts sad hub portion to increase the rigidity and biasing force of said side wall; and a tether affixed at one end to said guard housing and at its other end to said needle handle and of a length sufficient to permit the needle end to be withdrawn from said catheter hub but insufficient to permit the needle end to be withdrawn from the open end of said base portion whereby the needle end is maintained within said guard housing to prevent inadvertent puncture therefrom.

15. Apparatus of claim 14 wherein said tether means is a plastic ribbon having a discrete width and formed as a single coil when said apparatus is in its initial position.

* * * * *